United States Patent
Tokusumi et al.

(10) Patent No.: US 6,746,860 B1
(45) Date of Patent: Jun. 8, 2004

(54) PARAMYXOVIRUS VECTORS USED FOR TRANSFER OF FOREIGN GENES

(75) Inventors: Tsuyoshi Tokusumi, Ibaraki (JP); Akihiro Iida, Ibaraki (JP); Mamoru Hasegawa, Ibaraki (JP); Yoshiyuki Nagai, Tokyo (JP)

(73) Assignee: DNAVEC Research, Inc., Tsukuba (*) Notice: Subject to any disclaimer, the term of this patent is extended or adjusted under 35 U.S.C. 154(b) by 0 days.

(21) Appl. No.: 09/702,498

(22) Filed: Oct. 31, 2000

(30) Foreign Application Priority Data

May 18, 2000 (JP) ......................................... 2000/152726

(51) Int. Cl.$^7$ ............................ C12N 7/01; C12N 15/00; C07H 21/04; A01H 43/04
(52) U.S. Cl. ................................ 435/235.1; 435/320.1; 514/44; 536/23.72
(58) Field of Search .......................... 435/235.1, 320.1, 435/91.41; 536/23.1, 23.72; 514/44

(56) References Cited

U.S. PATENT DOCUMENTS 6,033,886 A * 3/2000 Conzelmann et al. ..... 435/172.3

FOREIGN PATENT DOCUMENTS

| EP | 0 702 085 A1 | * | 3/1996 |
| EP | 0863202 A1 | | 9/1998 |
| EP | 0864645 A1 | | 9/1998 |
| EP | 1 067 179 A1 | | 1/2001 |
| WO | WO 01/04272 A1 | | 1/2001 |
| WO | WO 01/20989 A1 | | 3/2001 |

OTHER PUBLICATIONS

Fields et al. Virology, 3rd edition. vol. 1. Philadelphia. Lippencott Williams and Wilkins Publishers. 1996, pp. 1314.*
Tokusumi et al. May 31–Jun. 4, 2000. The Third Annual Meeting of the American Society of Gene Therapy, Program 890.*
Kato et al. Journal of Virology. 1999; 73 (11): 9237–9246.*
Hasan et al. Journal of General Virology. 1997; 78: 2813–2820.*
Calain et al., "The Rule of Six, a Basic Feature for Efficient Replication of Sendai Virus Defective Interfering RNA," *J. Virology* 67:4822–4830 (1993).
Conzelmann et al., "Genetic manipulation of non–segmented negative–strand RNA viruses," *J. Gen. Virology* 77:381–389 (1996).
Hurwitz et al., "Intranasal Sendai virus vaccine protects African green monkeys from infection with human parainfluenza virus–type one," *Vaccine* 15:533–540 (1997).
Metsikkö et al., "Role of Heterologous and Homologous Glycoproteins in Phenotypic Mixing between Sendai Virus and Vesicular Stomatitis Virus," *J. Virology*, 63:5111–5118 (1989).
Schnell et al., "Infectious rabies from cloned cDNA," *EMBO Journal* 13:4195–4203 (1994).
Yonemitsu et al., "Gene therapy in vascular surgery comes of age," *Surgery* 131:S261–S268 (2002).
Tokusumi et al., "Cytoplasmic RNA Vector Equipped with a Unique Control System for Gene Expression," The Third Annual Meeting of the American Society of Gene Therapy, Program No. 890 (2000).
Kato et al., "Sendai Virus Gene Start Signals Are Not Equivalent in Reinitiation Capacity: Moderation at the Fusion Protein Gene," J. Virol. 73:9237–9246 (1999).
Hirata et al., "Improvement of Reconstitution Efficiency of Sendai Virus Vectors," The 48$^{th}$ Meeting of the Japanese Society for Virology, Abstract 12pm105 (2000).
Li et al., "Generation of a Sendai Virus Vector Defective in H and N Genes," The 48$^{th}$ Meeting of the Japanses Society for Virology, Abstract 12pm106 (2000).
Tokusumi et al., "An Unique Control System for Foreign Gene Expression by Cytoplasmic RNA Vector," The 6$^{th}$ Annual Meeting of the Japan Society of Gene Therapy, Abstract 114 (2000).

* cited by examiner

*Primary Examiner*—Mary E. Mosher
*Assistant Examiner*—Shanon Foley
(74) *Attorney, Agent, or Firm*—Clark & Elbing LLP

(57) ABSTRACT

A paramyxovirus vector capable of Extransfecting foreign genes and having a replication capacity, is provided. A Sendai virus vector comprising a foreign gene can be constructed by inserting a foreign gene between the viral genes of the Sendai virus genome. These Sendai viruses have a replication capacity and express the foreign gene in transfected cells. The expression level of the foreign gene is higher towards the 3' end of negative strand RNA, and especially, a high level of expression is obtained when the foreign gene is inserted before the NP gene, and between P gene and M gene. Conversely, the expression decreases towards 5' end of negative strand RNA, and especially, a relatively low level of expression is obtained when the when the foreign gene is inserted between HN gene and L gene, and between F gene and HN gene. Thus, the vector of the invention enables the regulation of the expression level of a foreign gene. The vector is useful for gene therapy due to its safety, high gene transfer efficiency, and capacity to express a foreign gene at a high level.

9 Claims, 7 Drawing Sheets

▲ novel NotI site (A)

(B)

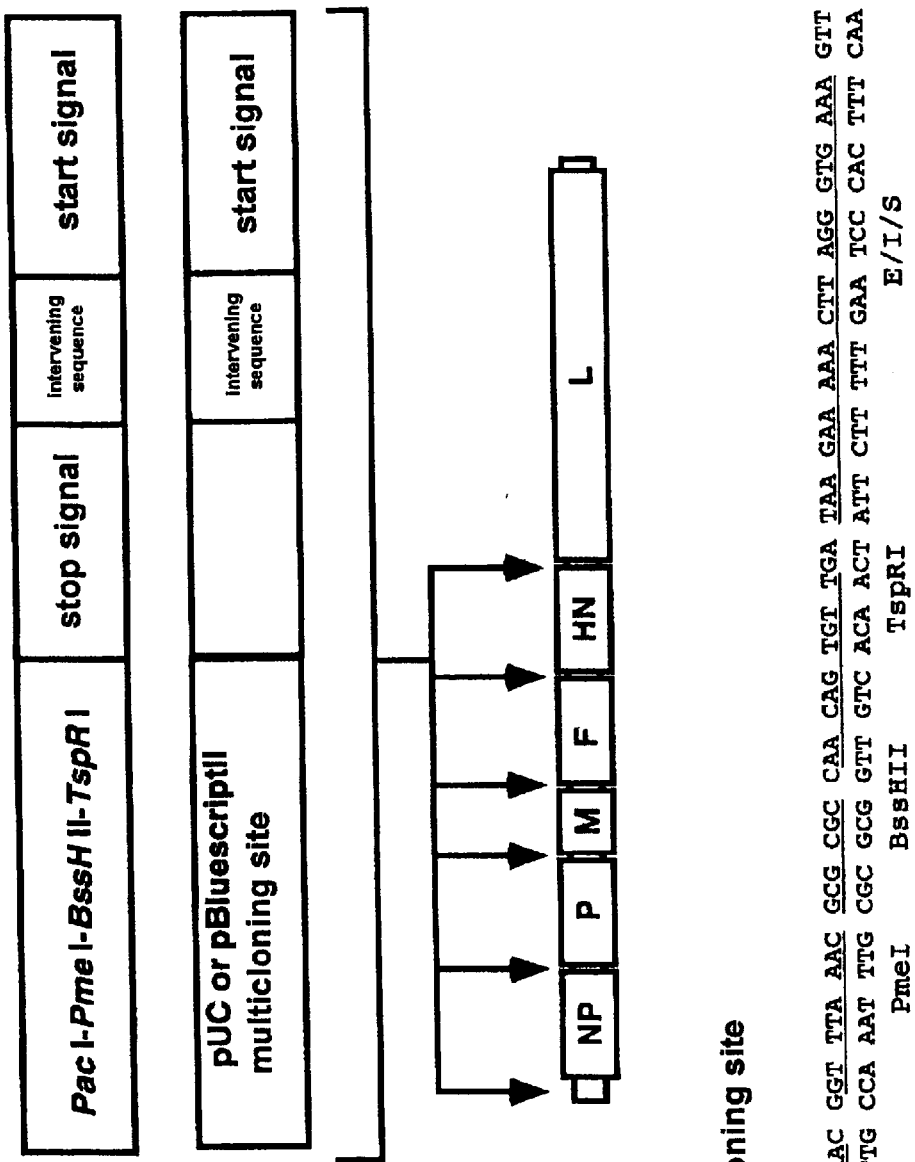

PARAMYXOVIRUS VECTORS USED FOR TRANSFER OF FOREIGN GENES

CROSS-REFERENCE TO RELATED APPLICATIONS

This application claims benefit of Japanese patent application JP 2000/152726 filed May 18, 2000.

FIELD OF THE INVENTION

The present invention relates to a paramyxovirus vector capable of transferring foreign genes and having a replication capacity.

BACKGROUND OF THE INVENTION

Until now, most of the approaches of clinical studies pertaining to gene therapy have utilized viral vectors such as retroviruses, adenoviruses, and adeno-associated viruses. These gene therapy vectors have limitations in gene transfer efficiency and continuous expression. Furthermore, the vectors themselves may have cytotoxicity, immunogenicity, and such problems are crucial when it comes to the medical application of these vectors (Lamb, R. A. & Kolakofsky, D., Paramyxoviridae: the viruses and their replication. in Fields Virology, 3rd edn, (Edited by B. N. Fields, D. M. Knipe & P. P. Howley) pp.1177–1204 (Philadelphia, Lippincott-Raven. (1996)). As a solution, novel vectors based on lentivirus and HSV have been proposed, and research is also being vigorously carried out to modify existing vectors. However, all these vectors exist in the form of DNA within the nucleus, throughout their life cycles. Therefore, it is difficult to overcome concerns of safety regarding random interactions with the chromosomes of the patient.

Rapid progress of reverse genetics technology is beginning to enable the development of vectors based on RNA viruses, which had long been delayed. Recombinant RNA vectors have a high gene transfer efficiency and expression capacity, and therefore, are highly potential vectors for gene therapy (Roberts, A. & Rose, J., K., Virology 247,1–6 (1998); Rose, J., Proc. Natl. Acad. Sci. USA 94, 14998–15000 (1996); Palese, P. et. al., Proc. Natl. Acad. Sci. USA 93, 11354–11358 (1996)). The paramyxovirus vectors that comprise negative strand RNA in the genome have several characteristics that significantly differ from retroviruses, DNA viruses, or plus strand RNA viruses. This genome or antigenome does not directly function as mRNA, and cannot initiate protein synthesis and genome replication of the virus. The RNA genome and antigenome of the virus consistently exists in the form of a ribonucleoprotein complex (RNP), and therefore problems of antisenses observed in plus strand RNA viruses, such as the inhibition of the assembly of genome towards RNP due to the hybridization of mRNAs to complementary naked genomic RNA, rarely occur. These viruses have their own RNA polymerase, and the transcription of viral mRNA or viral genome replication is carried out using the RNP complex as template. Worthy of special notice is the fact that negative strand RNA (nsRNA) viruses proliferate only within the cytoplasm of host cells, and since they do not have a DNA phase, they are not integrated into chromosomes. Furthermore, homologous recombination between RNAs has also not been observed. These features contribute largely to the stability and safety of negative strand RNA viruses as gene expression vectors.

Among the negative strand RNA viruses, the inventors have been focusing their attention on Sendai virus (SeV) that is not pathogenic towards humans, particularly the Z strain that is especially avirulent. SeV is a non-segmented negative strand RNA virus belonging to Paramyxoviruses, and is a type of murine parainfluenza virus. This virus attaches to the host-cell membrane via hemagglutinin-neuraminidase (HN) and fusion protein (F), which are two envelope glycoproteins, initiates membrane fusion, releases its own RNA polymerase and the RNA genome that exists in the form of ribonucleoprotein (RNP) complex into the cytoplasm, and carries out mRNA transcription and genome replication of the virus there (Bitzer, M. et al., J. Virol. 71(7): 5481–5486, 1997). The viral envelope protein F is synthesized as a non-active pre-protein ($F_0$), is cleaved into F1 and F2 through proteolytic cleavage by trypsin (Kido, H. et al., Biopolymers (Peptide Science) 51(1): 79–86, 1999), and turns into an active protein causing membrane fusion. This virus is said to be non-pathogenic towards humans. Moreover, a laboratory-attenuated strain (Z strain) has also been isolated, which only induces a slight pneumonia in rodents, its natural hosts. This strain is widely used as a research model for molecular-level studies in the transcription/replication mechanisms of paramyxoviruses, and has also been used in the preparation of hybridomas. Apart from a high safety, this virus shows a high production titer of $10^9$ to $10^{11}$ pfu/ml in cell lines and hen-eggs. In one recent successful recovery system from negative strand RNA virus cDNA, Sendai viruses showed an especially high reconstitution efficiency rate. In recombinant wild-type viruses transfected with foreign genes, the capacity to express the foreign gene efficiently as well stably, is gaining wide attention.

Even though Sendai viruses having a foreign gene upstream of the NP gene have been known, it was not known how the viral reconstitution and foreign gene expression will be affected when the foreign gene was inserted into a site other than the above.

SUMMARY OF THE INVENTION

An object of the present invention is to provide a paramyxovirus vector capable of transferring foreign genes and having a replicating capacity.

The inventors constructed viral vector DNA, in which a foreign gene was inserted to a site other than the upstream of the NP gene of the Sendai virus, and examined viral reconstitution and the expression level of the foreign gene. Namely, a new restriction enzyme site for inserting the foreign gene was introduced between the start signal and ATG translation start signal of each gene encoding viral proteins of Sendaivirus (SeV) full-length cDNA. A foreign gene (human secreted alkaline phosphatase (SEAP) gene) was inserted into this restriction enzyme site, and when reconstitution of the Sendai virus was conducted using LLC-MK2 cells, it was seen that only Sendai viruses having the capacity to proliferate were reconstituted. These viruses were amplified within hen-eggs to prepare a viral stock solution. These virus titers were combined and infected into LLC-MK2 cells, and the expression level of the foreign gene was determined to find that foreign gene expression is seen in all cases examined where the foreign gene was inserted into different sites. The foreign gene expression was relatively high when it was inserted between NP gene and P gene, or between P gene and M gene, and it was revealed that the foreign gene expression dropped as the site of insertion neared the downstream (5' side of the negative strand) of the genome.

These results suggest that it is possible to obtain a relatively high foreign gene expression by placing the foreign gene downstream of the NP gene or the P gene, and that it is possible to decrease the expression level by placing the foreign gene towards the downstream of the genome. Based on these findings, it is possible to regulate the expression level of the foreign gene within the vector, by inserting the foreign gene into the upstream of the genome, namely, in the 3' side of the negative strand genome, to obtain a high expression of the foreign gene. Conversely, when a high expression is not preferable, such as when the gene is cytotoxic, the foreign gene can be inserted downstream of the genome, namely, in the 5' side of the negative strand genome. The paramyxovirus vector of the invention is useful in the expression of foreign genes in vivo and in vitro, and would especially be applied in gene therapy taking advantage of the outstanding features of paramyxoviruses.

Though problems regarding genomic stability may be pointed out in RNA viruses, results of heterologous gene expressions using SeV vector showed that there were hardly any nucleotide mutations even when the virus was serially passaged over several generations, and that it is possible to stably express the inserted heterologous genes over a long period of time (Yu, D. et al. Genes cells 2, 457–466 (1997)). Vectors based on this negative strand RNA viral replicons have several merits owing to their features, such as genomic stability, flexibility of packaging and size of the transfected gene due to not having capsid structure proteins, when compared to virus vectors based on replicons of already-successful positive strand RNA viruses, such as Semliki forest virus or Sindbis virus. At least 4 kbp of foreign DNA can be introduced into the replicable Sendai virus vector, and it may be also possible to simultaneously express more than two types of genes by adding a transcription unit. Vectors based on this Sendai virus replicon is expected to be continuously expressed since the replicated virus will re-infect surrounding cells, and the replicated RNP, multi copied in the cytoplasm of the infected cells, will be distributed to daughter cells following cell division. Moreover, the vector of the present invention could have an extremely broad tissue coverage and be high in application capacity since Sendai virus vectors are highly efficiently introduced into hematocytic cells, especially, granulocytic cells, and also to c-kit positive primitive cells.

Namely, the present invention relates to a paramyxovirus vector capable of transferring a foreign gene and having the capacity to replicate, and more specifically relates to, (1) a replicable paramyxovirus vector carrying a foreign gene, wherein the foreign gene is located downstream of the genes encoding viral proteins in the negative strand genomic RNA contained within said vector, (2) a replicable paramyxovirus vector carrying a foreign gene, wherein said vector is selected from the group consisting of the vectors of (a) to (f) below, (a) a vector in which the foreign gene is inserted between the $1_{st}$ gene encoding a viral protein and the $2^{nd}$ gene encoding a viral structure protein from the 3' end of the negative strand genomic RNA contained within the vector, (b) a vector in which the foreign gene is inserted between the $2^{nd}$ gene encoding a viral protein and the $3^{rd}$ gene encoding viral structure protein from the 3' end of the negative strand genomic RNA contained within the vector, (c) a vector in which the foreign gene is inserted between the $3^{rd}$ gene encoding a viral protein and the $4^{th}$ gene encoding viral structure protein from the 3' end of the negative strand genomic RNA contained within the vector, (d) a vector in which the foreign gene is inserted between the $4^{th}$ gene encoding a viral protein and the $5^{th}$ gene encoding viral structure protein from the 3' end of the negative strand genomic RNA contained within the vector, (e) a vector in which the foreign gene is inserted between the $5^{th}$ gene encoding a viral protein and the $6^{th}$ gene encoding viral structure protein from the 3' end of the negative strand genomic RNA contained within the vector, (f) a vector in which the foreign gene is inserted between the $6^{th}$ gene encoding a viral protein from the 3' end of the negative strand genomic RNA contained within the vector, and the trailer sequence, (3) the vector of (2), wherein the $1^{st}$ to $6^{th}$ genes encoding viral proteins from the 3' end of the negative strand genomic RNA contained within the vector are, NP gene, P gene, M gene, F gene, HN gene, and L gene, in their order, (4) a DNA corresponding to the negative strand genomic RNA contained in the paramyxovirus vector of (1), or their complementary strands, (5) a DNA corresponding to the negative strand genomic RNA contained in replicable paramyxovirus vector or its complementary strand, wherein said DNA comprises a cloning site for inserting a foreign gene downstream of the genes encoding viral proteins, (6) a DNA corresponding to the negative strand genomic RNA contained in replicable paramyxovirus vector or its complementary strand, wherein said DNA is selected from the group consisting of the DNAs of (a) to (f) below, (a) a DNA comprising a cloning site for inserting a foreign gene between the $1^{st}$ and $2^{nd}$ genes encoding viral proteins from the site equivalent to the 3' end of the negative strand genomic RNA, (b) a DNA comprising a cloning site for inserting a foreign gene between the $2^{nd}$ and $3^{rd}$ genes encoding viral proteins from the site equivalent to the 3' end of the negative strand genomic RNA, (c) a DNA comprising a cloning site for inserting a foreign gene between the $3^{rd}$ and $4^{th}$ genes encoding viral proteins from the site equivalent to the 3' end of the negative strand genomic RNA, (d) a DNA comprising a cloning site for inserting a foreign gene between the $4^{th}$ and $5^{th}$ genes encoding viral proteins from the site equivalent to the 3' end of the negative strand genomic RNA, (e) a DNA comprising a cloning site for inserting a foreign gene between the $5^{th}$ and $6^{th}$ genes encoding viral proteins from the site equivalent to the 3' end of the negative strand genomic RNA, (f) a DNA comprising a cloning site for inserting a foreign gene between the $6^{th}$ gene coding a viral protein from the site equivalent to the 3' end of the negative strand genomic RNA and the trailer sequence, (7) the DNA of (6), wherein the $1^{st}$ to $6^{th}$ genes encoding viral proteins from the site equivalent to the 3' end of the negative strand genomic RNA contained within the vector are, NP gene, P gene, M gene, F gene, HN gene, and L gene, in their order, (8) a vector DNA carrying the DNA of (4) in an expressible manner, and, (9) the vector DNA of (8), which carries positive strand genomic RNA in an expressible manner.

"Viral vector" as used herein indicates virions capable of transferring nucleic acid molecules into hosts. Paramyxoviruses in the present invention mean viruses or their derivatives belonging to the family Paramyxoviridae. Paramyxoviruses applicable in the present invention are, for example, parainfluenza virus type I including Sendai virus and human HA2, etc., parainfluenza virus type II including monkey SV5 and SV41, as well as human CA, etc., parainfluenza virus type III including bovine SF and human HA1, etc., parainfluenza virus type IV (including A subtype and B subtype), mumpus virus, Newcastle virus, and other various paramyxoviruses. The virus of the invention is more preferably a Sendai virus. These viruses may be natural strains, mutant strains, strains passaged in the laboratory, and man-made strains. Incomplete viruses, such as the DI particles (J. Virol. 68, 8413–8417 (1994)), etc., synthesized oligo nucleotides, and such may also be used as materials to prepare the viral vector of this invention.

Genes encoding the paramyxovirus protein include, NP, P, M, F, HN, and L genes. "NP, P, M, F, HN, and L gene" refer to nucleocapsid, phospho, matrix, fusion, hemagglutinin-neuraminidase, and large protein encoding gene, respectively. The genes in each virus belonging to paramyxovirus sub-genus are generally indicated as below. Generally, NP gene may also be indicated as "N gene."

| Respirovirus genus | NP | P/C/V | M | F | HN | — | L |
| Rubullavirus genus | NP | P/V | M | F | HN | (SH) | L |
| Morbillivirus genus | NP | P/C/V | M | F | H | — | L |

For example, the accession numbers of the nucleotide sequence database of all genes of the Sendai virus classified into Respirovirus of Paramyxoviridae are, for the NP gene, M29343, M30202, M30203, M30204, M51331, M55565, M69046, X17218, for the P gene, M30202, M30203, M30204, M55565, M69046, X00583, X17007, X17008, for the M gene, D11446, K02742, M30202, M30203, M30204, M69046, U31956, X00584, X53056, for the F gene, D00152, D11446, D17334, D17335, M30202, M30203, M30204, M69046, X00152, X02131,for the HN gene, D26475, M12397, M30202, M30203, M30204, M69046, X00586, X02808, X56131, for the L gene, D00053, M30202, M30203, M30204, M69040, X00587, X58886.

"Having a replication capacity" or "being replicable" means that when the viral vector infects a host cell, the virus is replicated within said cell, and infective virions are produced. Also, in the present invention, "DNA" includes single-stranded and double-stranded DNA.

BRIEF DESCRIPTION OF THE DRAWINGS

FIG. 7 shows the structure of the multicloning site. The nucleotide sequence show examples of the multicloning site comprising a restriction enzyme site PacI-PmeI-BssHII-TspRIa and E/I/S sequence.

DETAILED DESCRIPTION OF THE INVENTION

Figure 1:
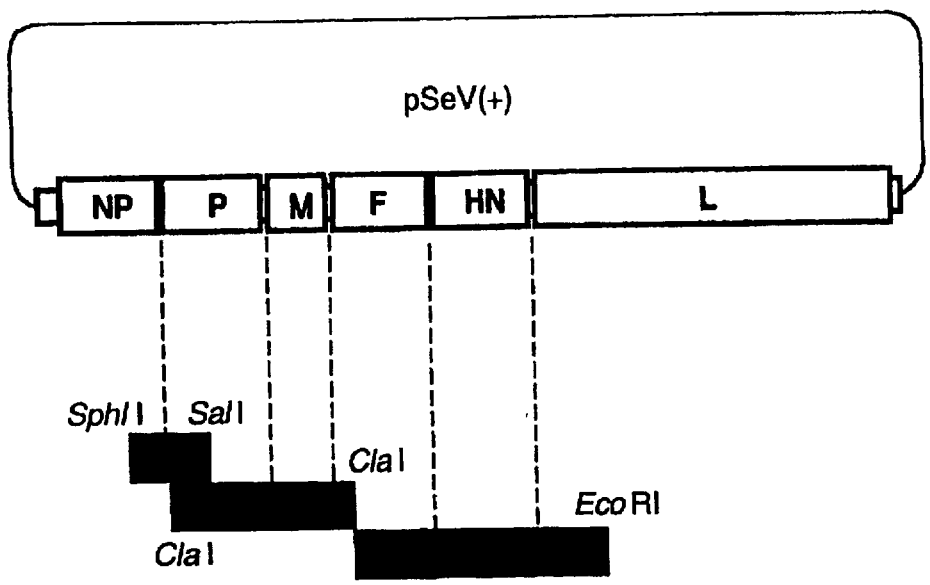
FIG. 1 shows the subcloning of Sendai virus genomic cDNA fragment (A) and the structures of five types of Sendai virus genomic cDNA constructed by inserting a new NotI site (B).
Figure 1:
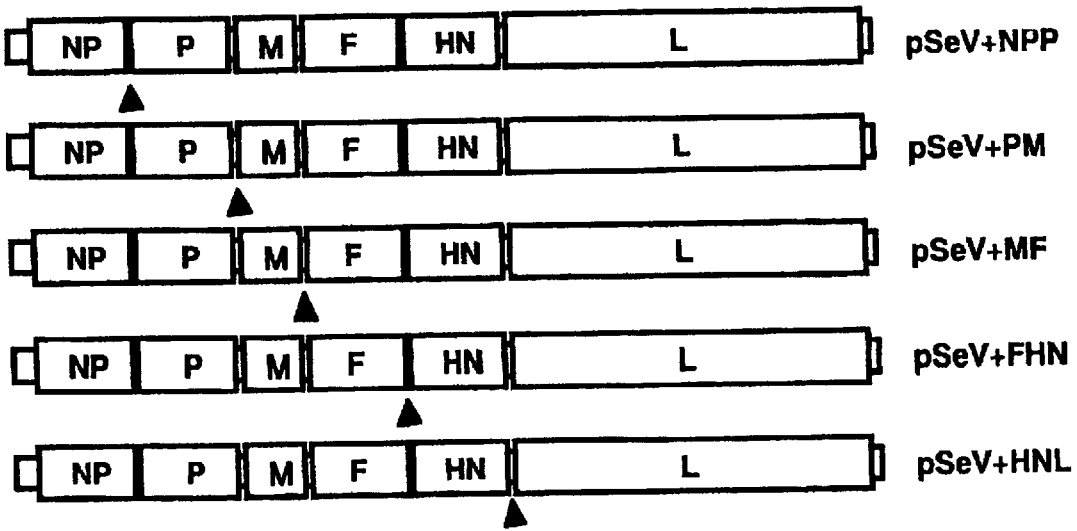

Paramyxoviruses generally contain a complex (ribonucleoprotein; RNP) comprised of RNA and proteins within their envelope. RNA contained in RNP are single-stranded RNA of the negative strand (minus strand), the paramyxovirus genome. The complex is formed when NP, P, and L proteins bind to this RNA. The RNA contained in this RNP becomes the template for the transcription and replication of the viral genome (Lamb, R. A., and D. Kolakofsky, 1996, Paramyxoviridae: The viruses and their replication. pp.1177–1204. In Fields Virology, 3rd edn. Fields, B. N., D. M. Knipe, and P. M. Howley et al. (ed.), Raven Press, New York, N.Y.). The RNP complex replicates autonomously within cells, to increase copies of genes (RNA contained in the complex). Thus, a high foreign gene expression is facilitated by a vector having the foreign gene.

Normally, the viral vector of the present invention can be prepared by: (a) transcribing vector DNA corresponding paramyxovirus-derived negative strand single-stranded RNA or its complementary strand (positive strand) into cells (helper cells) expressing NP, P, and L proteins, (b) culturing said cells, and (c) recovering virions from the culture supernatant. RNA transcribed from vector DNA, form an RNP complex with NP, L and P proteins, and furthermore, forms virions encompassed by an outer shell containing envelope proteins.

DNA (vector DNA) expressed within helper cells, corresponds to the minus strand (negative strand) of the genome or its complementary strand (positive strand RNA). For example, DNA corresponding to negative strand single-stranded RNA or its complimentary strand (positive strand) is ligated downstream of the T7 promoter, and transcribed to RNA by T7 RNA polymerase. Alternatively, RNA transcribed in vitro may be transfected to helper cells. The strand transcribed within cells, may be a positive strand or a negative strand of the virus genome, but it is preferable that a positive strand be transcribed in order to enhance the reconstitution efficiency.

In the case of the Sendai virus (SeV), the genome size of the natural virus is app. 15,000 nucleotides, and in the negative strand, following the 3' short reader sequence, six genes encoding NP (nucleocapsid), P (phospho), M (matric), F (fusion), HN (hemagglutinin-neuraminidase), and L (large) proteins are lined, with a short 5' trailer region in the other end. As long as the ability to replicate is maintained, a part of the genes may be deficient, and the configuration of these genes may not be the same as the wild type. Since M, HN, and F proteins are not needed for RNP formation, RNP is constituted by transcribing this genomic RNA (positive strand or negative strand) under the presence of NP, P, and L proteins. Infectious virions are constituted from this RNP. The reconstitution of the vector could be carried out within LLC-MK2, for example. NP, P, and L proteins can be supplied by transfecting expression vectors containing each gene into cells. Also, each gene may be incorporated into the chromosomes of host cells. NP, P, and L genes expressed to form RNP do not need to be completely equivalent to NP, P, and L genes contained in the vector genome. Namely, even if the amino acid sequence of proteins encoded by these genes is not the same as the amino acid sequence of proteins encoded by RNP genome, it forms RNP together with genomic RNA, and as long as it has the activity to induce gene expression from this RNP, mutations may be added, or these genes may be substituted by homologous genes of another virus. If RNP is formed, NP, P, and L genes will be expressed from this RNP, RNP will replicate autonomously within cells, and viral vectors will be produced together with the envelope protein.

The virus produced is re-infected into cultured cells, hen-egg, individuals (for example, a mammal such as a mouse), and so on, to amplify or passage the virus. The viral vector of this invention can be amplified by re-transfecting the RNP formed at the reconstitution of the virus into host cells such as LLC-MK2. This process includes the steps of: (a) transfecting a complex comprised of paramyxovirus-derived negative strand single-stranded RNA, NP, P, and L protein; and (b) culturing the cells, and (c) recovering virions from the culture supernatant.

RNP can be transfected into cells by forming a complex to together with LipofectAMINE or polycationic liposome. Specifically, various transfection reagents may be used. For example, DOTMA (Boehringer), Superfect (QIAGEN #301305), DOTAP, DOPE, DOSPER (Boehringer #1811169), and such can be given. To prevent degradation within the endosome, chloroquine may also be added (Calos, M. P., 1983, Proc. Natl. Acad. Sci. USA 80: 3015).

At the time of virus reconstitution, an envelope protein other than that encoded by genomic RNA may be expressed within cells. As such proteins, envelope proteins of other viruses, for example, G protein (VSV-G) of vesicular stomatitis virus (VSV) can be given. The paramyxovirus vectors of the present invention, may be vectors comprising envelope proteins deriving from viruses other than those of genomic origin, such as the VSV-G protein. Other than viral envelope proteins, for example, chimera proteins, and such, that comprise adhesion factors, ligands, receptors, and such, which are capable of the adhesion onto specific cells, and also comprising polypeptides of viral envelope origin in intracellular regions, may be used. Thereby, vectors targeting specific tissues could be created. These may be encoded in the virus genome, or may be supplied by the expression of genes other than the genome (e.g. expression vectors or genes of host chromosome) at the time of viral vector reconstitution.

In the viral vector of the invention, the viral genes contained in the vector may be modified genes, in order to reduce immunogenicity, or to enhance RNA transcription efficiency and replication efficiency. Specifically, the transcription or replication functions can be enhanced by modifying, for example, at least one of the replication factors, NP gene, P gene, and L gene. The HN protein, which is one of the structural proteins, has both the activities of the hemagglutinin and neuraminidase. For example, if the activity of the former can be weakened, the stability of the virus within blood can be enhanced, and if the activity of the latter can be modified, it will be possible to regulate the infectivity. The fusion ability of membrane fusion liposomes could be regulated by modifying the F protein involved in membrane fusion. Furthermore, since the analysis of antigen presenting epitopes of F protein and HN protein that could become cell surface antigen molecules became possible through the establishment of the reconstitution system, using this analysis, it is possible to prepare Sendai viruses with a weak antigen presentation ability.

The viral vector of the invention carries a foreign gene within its negative strand single-stranded RNA, or comprises a site for inserting a foreign gene. A desired gene one would like to express within a target cell can be used as the foreign gene. For example, for objectives such as gene therapy, a therapeutic gene against a target disease is inserted into the DNA of said viral vector. The foreign gene can be inserted downstream of each viral gene (NP, P, M, F, HN, and L gene) (refer Examples). Herein, "downstream" means, 3' flanking region of the sense strand encoding proteins. Namely, for a negative strand RNA (or DNA), downstream of a gene refers to the 5' flanking region of said gene, and for a positive strand RNA (or DNA), it is the 3' flanking region of said gene.

For example, in the wild-type paramyxovirus, the viral genes are located in the order of NP, P, M, F, HN, and L from the 3' side of the negative genome, but for the vector of the present invention, the location may be any other as well. In order not to disturb the expression of genes existing prior and subsequent to the foreign gene, a suitable E-I-S sequence (transcription stop sequence—intervening sequence—transcription start sequence) or a portion of it is inserted prior and subsequent to the foreign gene. For example, when introducing a foreign gene into the DNA corresponding to the Sendai virus genome, it is preferable to insert a sequence with a multiple of six bases between the genes encoding the viral proteins (J. Virol., Vol. 67, No. 8, 1993, 4822–4830). The expression of the inserted foreign gene can be regulated by the type of the transcription start sequence added to the 5' side (the head) of the foreign gene. The regulation can also be done by the site to which the gene is inserted, or by the nucleotide sequence prior and subsequent to the foreign gene.

As shown in Examples, in the Sendai virus, the expression level of the inserted gene elevates as the position of insertion nears the 3' end of the negative strand RNA (in the gene configuration upon the genome of the wild-type virus, as it nears the NP gene). In order to obtain a high foreign gene expression, the foreign gene is inserted downstream (namely, between the $1^{st}$ and $2^{nd}$ genes) of the gene that is most upstream (at the 3' side of the negative strand) among the genes encoding viral proteins. Specifically, in the gene configuration of the wild-type genome, the foreign gene is inserted downstream (for the negative strand, 5' flanking region of the NP gene) of the NP gene, in other words, between the NP and P genes. Alternatively, a relatively high expression can also be obtained by inserting the foreign gene between the $2^{nd}$ and $3^{rd}$ genes from the upstream of the genes encoding viral proteins. In this case, in the gene configuration of the wild-type genome, the foreign gene is inserted downstream (for the negative strand, 5' flanking region of the P gene) of the P gene, in other words, it is preferable to insert the foreign gene between the P gene and the M gene. Conversely, the expression level of the inserted gene declines as the position of insertion nears the 5' end of the negative strand RNA (in the gene configuration upon the genome of the wild-type virus, as it nears the L gene). In order to suppress the expression of a foreign gene, the foreign gene is inserted: into the downstream (namely, between $1^{st}$ gene from the 5' end of the negative strand and the trailer sequence; in the wild-type genome, between the $6^{th}$ gene from the 3' side and the trailer sequence) of the gene encoding the viral protein, which is most downstream (5' side of the negative strand) of the genes encoding the viral proteins; or into the upstream (namely, between the $1^{st}$ and $2^{nd}$ genes from the 5' side; in the wild-type virus genome, between the $5^{th}$ and $6^{th}$ genes from the 3' side). Specifically, in the wild-type genome gene configuration, the foreign gene is inserted downstream of the L gene (in the negative strand, 5' flanking region of the L gene) or into the upstream of the L gene (in the negative strand, 3' flanking region of the L gene), namely, between the L gene and trailer sequence or between the HN gene and the L gene, respectively. The expression can also be suppressed by inserting the foreign gene between the 4$^{th}$ and 5$^{th}$ genes from the upstream of the genes encoding viral proteins. In this case, in the wild type genome gene configuration, it is preferable to insert the foreign gene downstream of the F gene (in the negative strand, 5' flanking region of the F gene), in other words, between the F gene and HN gene. The vector of the invention may carry some other foreign gene in locations other than those into which the foreign gene is inserted.

The position into which the foreign gene is inserted, may be properly adjusted to facilitate a desired expression level of said gene, or to maximize the combination of the genes encoding viral proteins that exist prior and subsequent to the inserted gene.

To easily insert a foreign gene, a cloning site can be designed at the position of insertion. Typically, the cloning site can be a recognition sequence of a restriction enzyme. Preferably, a restriction enzyme site is designed, which is not a site that is present in the foreign gene to be inserted. As such a restriction enzyme, one that recognizes a long sequence, such as an 8 bp recognizing restriction enzyme, is preferable. As 8 bp recognizing restriction enzymes, for example, AscI (GG↓CGCGCC), FseI (GGCCGG↓CC), NotI (GC↓GGCCGC), PacI (TTAAT↓TAA), PmeI (GTTT↓AAAC), SfiI (GGCCNNNN↓NGGCC), SgfI (GCGAT↓CGC), SrfI (GCCC↓GGGC), Sse232I (CG↓CCGGCG), Sse8387I (CCTGCA↓GG), and SwaI (ATTT↓AAAT), and such can be given, but are not restricted thereto. The cloning site may be one that comprises several restriction enzyme recognition sequences, the so-called multicloning site. Also, it may be a sequence that is cleaved by an endonuclease other than a restriction enzyme. It is also possible to envisage inserting a foreign gene by recombination by making the cloning site be a recognition sequence of a recombinase. The designing of these sequences within the DNA corresponding to the viral genome, can be done by commonly known mutation induction methods. Furthermore, it is also conceivable to create a cloning site by segmenting the foreign gene inserting position beforehand. If the 5' end of the segmented vector DNA is dephosphorylated beforehand, the clone into which the foreign gene has been inserted can be preferentially generated. Also, if the 3' end of the fragmented vector DNA is single nucleotide blunt-ended at T, the foreign gene (where the blunt-end is A) amplified by PCR, can be easily cloned. When the vector DNA is a circular DNA as a plasmid, a high ligation efficiency can be obtained as both ends do not disengage even when the cloning site is segmented.

The insertion of a foreign gene into DNA (vector DNA) corresponding to the viral genome can be done as follows according to "Kato, A. et al., 1997, EMBO J. 16: 578–587 and Yu, D. et al., 1997, Genes Cells 2: 457–466".

First, a DNA sample containing the cDNA nucleotide sequence of a desired foreign gene is provided. The DNA sample is preferably one that can be verified to be a single plasmid by electrophoresis at a concentration of 25 ng/μl or more. The following is a description of inserting a foreign gene into the DNA corresponding to the viral genome using the NotI site. When a NotI site is contained within the objective cDNA nucleotide sequence, the nucleotide sequence is modified in a way that the encoded amino acid sequence is not changed, using site-specific mutagenesis, and such method, and the Not I site is preferably removed beforehand. A desired gene fragment is amplified by PCR and recovered from this sample. Both ends of the amplified fragment is made into NotI sites, and furthermore, in order to add a copy of the Sendai virus transcription stop sequence (E), intervening sequence (I) and transcription start sequence (S) (EIS sequence), forward side synthetic DNA sequence (sense strand) and reverse side synthetic DNA sequence (antisense strand) are prepared as a pair of primers containing NotI restriction enzyme cleavage site sequence, transcription stop sequence (E), intervening sequence (I), transcription start sequence (S), and a partial sequence of the objective gene.

For example, for the forward side synthetic DNA sequence, two or more arbitrary nucleotides (preferably, four nucleotides not containing NotI recognition site-derived sequences, such as GCG, and GCC, more preferably ACTT) are selected in the 5' side to ensure cleaving by NotI. Then, a NotI recognition site gcggccgc is added to the 3' side, and to the 3' side thereof, further nine arbitrary nucleotides or a number of nucleotides where multiples of six have been added to nine are attached, and to the 3' side thereof, an ORF sequence corresponding to app. 25 nucleotides from the initiation codon ATG of the desired cDNA including the initiation codon ATG, is added. The 3' end of the forward side synthetic oligo DNA is preferably selected from app. 25 nucleotides from the desired cDNA so that the last nucleotide become G or C.

For the reverse side synthetic DNA sequence, two or more arbitrary nucleotides (preferably, four nucleotides not containing NotI recognition site-derived sequences, such as GCG, and GCC, more preferably ACTT) are selected from the 5' side, and to the 3' side thereof, a NotI recognition site gcggccgc is added, and to the 3' side thereof, an oligo DNA insert fragment is added to control the length. The length of this oligo DNA is designed so that the sum of cDNA complementary strand nucleotide sequence and the EIS nucleotide sequence of the Sendai virus genome of Sendai virus origin described later on, becomes a multiple of six (the so-called "rule of six"; Kolakofski, D. et al., J. Virol. 72:891–899, 1998). Furthermore, the complementary strand sequence of the Sendai virus S sequence, preferably 5'-CTTTCACCCT-3' (SEQ ID NO:33), the complementary strand sequence of the I sequence, preferably, 5'-AAG-3', the complementary strand sequence of the E sequence, preferably 5'-TTTTTCTTACTACGG-3' (SEQ ID NO:34), is added to the 3' side of the insert fragment, and furthermore, to the 3' side thereof, a sequence, the length of which was selected so that the last nucleotide of the complementary strand of app. 25 nucleotides counted inversely from the end codon of a desired cDNA sequence becomes G or C, to make the 3' end of reverse side synthetic oligo DNA.

For PCR, the usual method that utilizes, for example, ExTaq polymerase (TaKaRa) can be used. Preferably, PCR is done using Vent polymerase (NEB), and after digesting the amplified objective fragment by NotI, it is inserted into the NotI site of plasmid vector pBluescript. The nucleotide sequence of the obtained PCR product is verified using a sequencer, and the plasmid having the correct sequence is selected. The insert fragment is excised from this plasmid using NotI, and cloned into the NotI site of a plasmid containing genomic cDNA. It is also possible to obtain recombinant Sendai virus cDNA by directly inserting the objective fragment into the NotI site without mediating the plasmid vector pBluescript.

DNA corresponding to the virus genome can be produced by: constructing vector DNA by ligating a suitable transcription promoter; transcribing this in vitro or in cells; reconstituting RNP under the presence of L, P, and NP proteins of the virus; and producing viral vectors containing this RNP. The reconstitution of viruses from viral vector DNA can be carried out according to commonly known methods (WO97/16539; WO97/16538; Durbin, A. P. et al., 1997, Virology 235: 323–332; Whelan, S. P. et al., 1995, Proc. Natl. Acad. Sci. USA 92: 8388–8392; Schnell. M. J. et al., 1994, EMBO J. 13: 4195–4203; Radecke, F. et al., 1995, EMBO J. 14: 5773–5784; Lawson, N. D. et al., Proc. Natl. Acad. Sci. USA 92: 4477–4481; Garcin, D. et al., 1995, EMBO J. 14: 6087–6094; Kato, A. et al., 1996, Genes Cells 1: 569–579; Baron, M. D. and Barrett, T., 1997, J. Virol. 71: 1265–1271; Bridgen, A. and Elliott, R. M., 1996, Proc. Natl. Acad. Sci. USA 93: 15400–15404.

To transfect vector DNA into cells, the following methods, (1) the method of preparing a DNA precipitate capable being incorporated by cells, (2) the method of producing a complex that is suitable for the incorporation by cells, which is also low-toxic and comprises DNA having a positive charge, (3) the method of instantly opening a hole sufficient enough for DNA molecules to pass through using an electric pulse.

Various transfection reagents could be used for (2). Examples are, DOTMA (Boehringer), Superfect (QIAGEN #301305), DOTAP, DOPE, DOSPER (Boehringer #1811169), etc. The transfection method using calcium phosphate can be given as an example for (1), and it is known that even though the DNA incorporated into cells by this method is taken up by phagocytic cellules, a sufficient amount enters the nucleus as well (Graham, F. L. and Van Der Eb, J., 1973, Virology 52: 456; Wigler, M. and Silverstein, S., 1977, Cell 11: 223). Chen and Okayama examined ways to optimize transfer techniques and report that 1) the best incubation conditions for the cells and precipitates are 2 to 4% $CO_2$, 35° C., 15 to 24 hr, 2) circular DNA has a higher activity than linear DNA, and 3) the optimal precipitate could be obtained when the DNA concentration of the precipitate mixture is 20 to 30 $\mu$g/ml (Chen, C. and Okayama, H., 1987, Mol. Cell. Biol. 7: 2745). The method of (2), is suitable for transient transfection. The method of transfection by preparing DEAE-dextran (Sigma #D-9885 M. W. $5\times10^5$) mixture by a desired DNA concentration ratio has been known. Chloroquine may also be added to enhance efficiency as most of the complexes are degraded inside endosomes (Calos, M. P., 1983, Proc. Natl. Acad. Sci. USA 80: 3015). Method of (3) is called electroporation and has a high versatility compared to methods of (1) and (2) as there is no cell selectivity. The efficiency is said to be good under optimal conditions of pulse current duration, form of pulse, the strength of the electric field (the gap between the electrodes, voltage), electric conductivity of the buffer, DNA concentration, and cell density.

Among the above three categories, the method of (2) is easy to handle, and many samples can be examined using a large number of cells, and therefore, the use of transfection reagents are appropriate for the present invention. Suitable is Superfect Transfection Reagent (QIAGEN, Cat No. 301305), or DOSPER Liposomal Transfection Reagent (Boehringer Mannheim, Cat No. 1811169).

Reconstitution from cDNA is specifically done as follows.

Monkey kidney derived cell line LLC-MK2 cells were cultivated until 70 to 80% confluency ($1\times10^6$ cells) in a 6-well plastic plate using 10% bovine fetal serum (FCS) and antibiotics (100 units/ml penicillin G and 100 $\mu$g/ml streptomycin) containing minimum essential medium (MEM). Then the cells are infected with T7 polymerase-expressing recombinant vaccinia virus vTF7-3 (Fuerst, T. R. et al., Proc. Natl. Acad. Sci. USA 83: 8122–8126, 1986, Kato, A. et al., Genes Cells 1: 569–579, 1996) inactivated by a 20 min UV irradiation treatment under the presence 1 $\mu$g/ml psoralen at 2PFU/cell. The amount of proralen added and the duration of UV irradiation can be suitably adjusted. After a one-hour infection, 2 to 60 $\mu$g, more preferably 3 to 5 $\mu$g of the above-mentioned recombinant Sendai virus cDNA is transfected into the cells by the lipofection method using plasmids (24–0.5 $\mu$g of pGEM-N, 12–0.25 $\mu$g of pGEM-P, and 24–0.5 $\mu$g of pGEM-L, more preferably 1 $\mu$g of pGEM-N, 0.5 $\mu$g of pGEM-P, and 1 $\mu$g of pGEM-L)(Kato, A. et al., Genes Cells 1:569–579, 1996) expressing viral proteins functioning in trans needed for the production of the full-length Sendai virus genome, together with Superfect (QIAGEN). The transfected cells are cultured in serum-free MEM containing desirably 100 $\mu$g/ml of rifampicin (Sigma) cytosine arabinoside (AraC), more preferably 40 $\mu$g/ml of cytosine arabinoside only, and the optimal concentration of the reagents are set so as to maximize the viral recovery rate and to minimize the toxicity due to the vaccinia virus (Kato, A. et al., 1996, Genes Cells 1: 569–579). After culturing about 48 to 72 hr following transfection, cells are collected, and freeze-thawing is repeated three times to lyze cells. The lysate is transfected into LLC-MK2 cells, and the cells are cultured. Alternatively, the culture supernatant is collected, this is added to the LLC-MK2 cell culture medium, and cultured for infection. The culture medium is collected after a 3 to 7 day culture. Alternatively, the collected cells may be co-cultured with other cells by culturing in layers. The virus titer contained in the culture supernatant could be determined by measuring haemagglutination activity (HA). HA could be determined by "end point dilution method" (Kato, A. et al., 1996, Genes Cells 1: 569–579). The obtained viral stock is stored at −80° C.

The recombinant Sendai viral vector of the invention can be made into a composition by diluting suitably using, for example, physiological saline and PBS, etc. When the recombinant viral vector of the invention is proliferated within hen-eggs, chorioallantoic fluid can also be contained. A composition comprising the recombinant viral vector of the invention may also contain a vehicle such as deionized water, 5% dextrose solution, and such physiologically acceptable vehicles. Furthermore, other than these, stabilizers, pesticides, and such may also be contained.

The host cells used for reconstitution are not restricted as long as the viral vector is reconstituted. For example, for the reconstitution of the Sendai virus, monkey kidney derived CV-I cells and LLC-MK2 cells, hamster kidney-derived BHK cells and such culture cells can be used. By expressing a suitable envelope protein in these cells, it is possible obtain infective virions comprising that envelope. Also, in order to obtain large amounts of the Sendai virus vector, the viral vector obtained from the above host can be infected into developing hen-eggs to amplify said vector. The method of producing viral vectors using hen-eggs has already been developed (Leading edge techniques protocol III in neuroscience research, edited by Nakanishi, et al., KOUSEISHA, Osaka, 1993, pp. 153–172). Specifically, for example, the fertilized eggs are moved to an incubator, and cultured for 9 to 12 days at 37° C. to 38° C. to grow the embryo. The Sendai viral vector is inoculated into the chorio-allantoic membrane cavity, the egg is incubated a few days to proliferate the viral vector. Conditions such as the culture duration changes according to the recombinant Sendai virus used. Then, the chorio-allantoic fluid containing the virus is collected. The separation and purification of the Sendai virus vector from the chorio-allantoic fluid is done according to the usual methods ("Virus Experiment Protocols" by Makoto Tashiro, edited by Nagai and Ishihama, Medical View, pp.68–73, (1995)).

If the viral vector is prepared using a therapeutic gene of a disease as the foreign gene, gene therapy can be done by administering this vector. A foreign gene anticipated to have a therapeutic effect or an endogenous gene whose supply within a patient's body is insufficient, can be expressed by both direct and indirect (ex vivo) administration. Since the viral vector of the invention is highly safe, and the foreign gene expression level is also high, a relatively large therapeutic effect can be expected even with a small amount of administration. The foreign gene is not restricted, and can be, in addition to nucleic acids encoding proteins, nucleic acids that do not encode proteins such as antisense and ribozymes, and such can also be used. If a gene encoding an antigen of a bacteria or virus the causes infectious diseases is used as the foreign gene, it will be possible to induce immunity in an animal to which the vector is administered. Namely, the vector can be used as a vaccine. Also, it is possible to use an antigen gene derived from viruses for which the need of a vaccine is high, for example, pathogenic paramyxoviruses such as, measles virus, mumps virus, etc.

When using as a vaccine, the viral vector of the invention can be applied against for example, cancer, infectious diseases, and other general diseases. For example, for anti-cancer therapy, a gene having the therapeutic effect can be expressed in antigen presenting cells (APC) such as cancer cells, or DC by using the vector of the invention. As such genes, tumor antigen Muc-1 or Muc-1-like mucin tandem repeat peptide (U.S. Pat. No. 5,744,144), melanoma gp100 antigen can be given. Such gene therapies have been suggested in a wide variety of cancers, such as breast cancer, colon cancer, pancreatic cancer, prostate cancer, lung cancer, etc. Cytokines may also be combined to enhance adjuvant effects. Such genes include, for example, i) combination of IL-2 and single-stranded IL-12 (Proc. Natl. Acad. Sci. USA 96(15): 8591–8596, 1999); ii) combination of IL-2 and interferon-γ (U.S. Pat. No. 5,798,100); iii) granulocyte colony stimulating factor (GM-CSF) used alone and; iv) combination of GM-CSF and IL-4 targeting therapy of brain cancers (J. Neurosurgery 90(6), 1115–1124 (1999)).

Vaccination for infectious diseases can be done by oral administration of the vector of the invention as it is or administration of the vector encompassed in polylactic acid-glycol copolymers (Kaneko, H. et al., Virology 267: 8–16 (2000)). Proteins encoded by the foreign gene include, for example, for influenza, the highly toxic strain H5N1-type envelope; for Japanese encephalitis, envelope chimera (Vaccine, vol. 17, No. 15–16, 1869–1882 (1999)); for AIDS, HIV gag or SIV gag protein (J. Immunology. (2000) vol. 164, 4968–4978), and HIV envelope protein; for cholera, for example, the β-subunit of cholera toxin (CTB) (Arakawa T, et al., Nature Biotechnology (1998) 16(10): 934–8, Arakawa T, et al., Nature Biotechnology (1998) 16(3): 292–7); for rabies, for example, glycoproteins of rabies virus (Lodmell DL et al., 1998, Nature Medicine 4(8): 949–52); for uterus cancer, capsid protein L1 of human papilomavirus 6-type (J. Med. Virol, 60, 200–204 (2000)) etc.

The application into general illnesses is also possible. For example in diabetes, the expression of a peptide of an insulin fragment is being carried out in the type I diabetes model (Coon, B. et al., J. Clin. Invest., 1999, 104(2):189–94).

When the need arises to suppress the proliferation of the viral vector after the completion of treatment or during treatment, RNA dependent RNA polymerase inhibitor can be administered to selectively suppress only the proliferation of the viral vector, without damaging host cells.

The present invention relates to a paramyxovirus vector capable of transferring foreign genes and having a replication capacity. The present invention enables the regulation of the expression level of a foreign gene. It is also possible to envisage the creation of a viral vector having foreign genes inserted to two or more sites. Since the Sendai virus has a high gene transfer efficiency in a wide variety of cell types and can express a foreign gene at a high level, the present invention is useful in, for example, gene therapy in which genes are introduced into the human body.

The present invention will be described in detail below with reference to examples, but is not construed to be limited thereto.

EXAMPLE 1

Regulation of gene expression level using the polarity effect in the Sendai virus 1. Construction of SeV Genomic cDNA A novel NotI site was inserted between the start signal and ATG translation start signal of each gene of cDNA of the Sendai virus (SeV) full-length genome, pSeV(+)(Kato, A. et al., Genes to Cells 1: 569–579, 1996). Specifically, as shown in FIG. 1 (A), each of the fragments: the fragment (2645 bp) in which pSeV(+) was digested by SphI/SalI, the fragment (3246 bp) digested by ClaI, and the fragment (5146 bp) digested by ClaI/EcoRI were separated by electrophoresis separately, the corresponding bands were excised, and collected/purified by QIAEXII Gel Extraction System (QIAGEN). The fragment digested by SphI/SalI, was ligated to LITMUS38 (NEW ENGLAND BIOLABS), and the fragments digested by ClaI and the fragment digested by ClaI/EcoRI were ligated to pBluescript II KS+ (STRATAGENE), and subcloned. Next, the QuikChange Site-Directed Mutagenesis kit (STRATAGENE) was used to introduce NotI site. Primers used for each introduction were as follows:

For between NP-P sense strand: 5'-ccaccgaccacacccagcggccgcgacagccacgg
  cttcgg-3'  (SEQ ID NO: 1), antisense strand: 5'-ccgaagccgtggctgtcgcggccgctgggtgt
  ggtcggtgg-3'  (SEQ ID NO: 2);

For between P-M sense strand: 5'-gaaatttcacctaagcggccgcaatggcagatat
  ctatag-3'  (SEQ ID NO: 3), antisense strand: 5'-ctatagatatctgccattgcggccgcttaggtga
  aatttc-3'  (SEQ ID NO: 4);

For between M-F sense strand: 5'-gggataaagtcccttgcggccgcttggttgcaaaact
  ctcccc-3'  (SEQ ID NO: 5), antisense strand: 5'-ggggagagttttgcaaccaagcggccgcaagggactt
  tatccc-3'  (SEQ ID NO: 6), For between F-HN sense strand: 5'-ggtcgcgcggtactttagcggccgcctcaaacaagcacaga
  tcatgg-3'  (SEQ ID NO: 7), antisense strand: 5'-ccatgatctgtgcttgtttgaggcggccgctaaagtaccgc
  gcgacc-3'  (SEQ ID NO: 8);

For between HN-L sense strand: 5'-cctgcccatccatgacctagcggccgcttcccattcac cctggg-3' (SEQ ID NO: 9), antisense strand: 5'-cccagggtgaatgggaagcggccgctaggtcatggatg ggcagg-3' (SEQ ID NO: 10).

As the template, the fragments sub-cloned above, namely for between NP-P, the SalI/SphI fragment, for between P-M and for between M-F, the ClaI fragment, for between F-HN and for between HN-L, the ClaI/EcoRI fragment, were used. The NcoI site was introduced according to the protocol accompanying QuikChange Site-Directed Mutagenesis kit. The introduced fragments were re-digested by enzymes, subcloned, collected/purified similarly, and assembled to cDNA of the original Sendai virus genome. As a result, five types of viral genomes, (pSeV(+)NPP, pSeV(+)PM, pSeV (+)MF, pSeV(+)FHN and pSeV(+)HNL) having a novel NotI site between each gene as shown in FIG. 1 (B) were constructed.

To insert the foreign gene, a DNA fragment to which "stop signal-intervening sequence-stop signal" has been added downstream of the foreign gene is inserted into the NotI site of the above-mentioned viral genomic cDNA. The foreign gene can be easily inserted into the multicloning site, for example, if a sequence (see FIG. 2) in which the multicloning site and the stop signal-intervening sequence-stop signal has been crammed into the two NotI sites is prepared beforehand.

Figure 3:
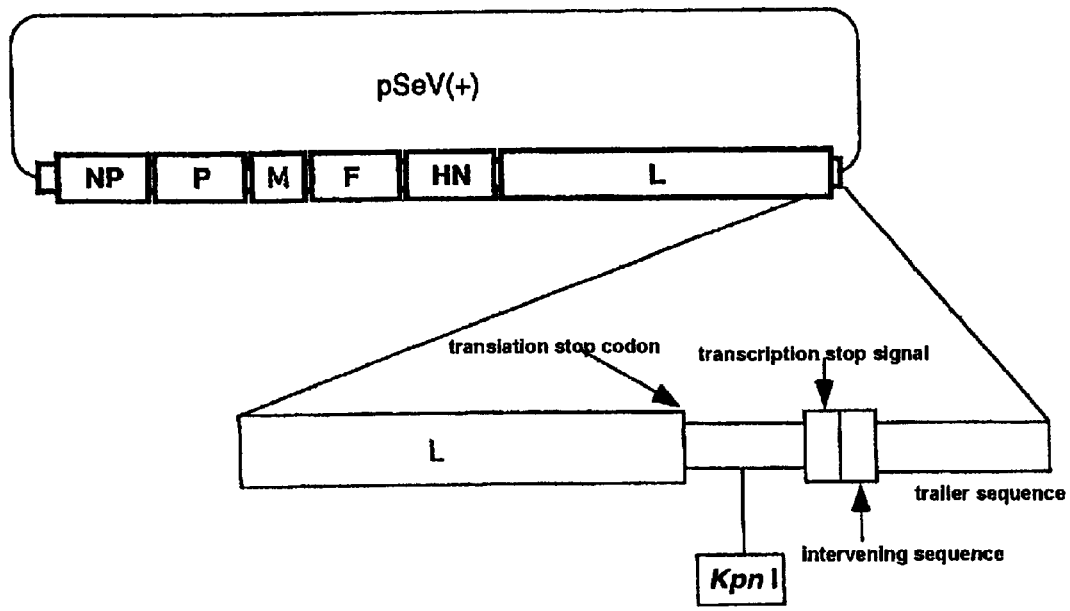
FIG. 3 shows the structure of Sendai virus genome that is downstream of the L gene (A), and the structure of DNA used for cloning to insert a foreign gene downstream of the L gene (B).
Figure 3:
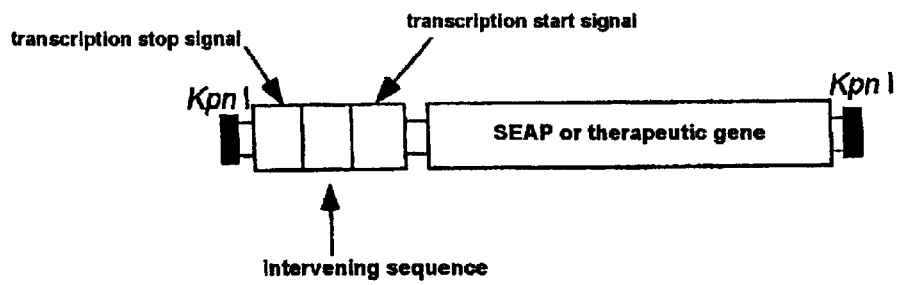

To insert the foreign gene downstream of the L gene, for example, in pSeV(+) or the desired SeV cDNA (pSeV18+, pSeV(+)NPP, pSeV(+)PM, pSeV(+)MF, pSeV(+)FHN and pSeV(+)HNL), and such mentioned above, the gene can be inserted into restriction enzyme KpnI site existing between the termination codon and transcription termination codon of the L gene (FIG. 3(A)). In this case, a KpnI site is added to both ends, and stop signal-intervening sequence-start signal is added to the 5' side of the foreign gene to be inserted by PCR. The added DNA is incorporated into SeV cDNA to obtain cDNA into which the foreign gene has been inserted downstream of the L gene.

Figure 2:
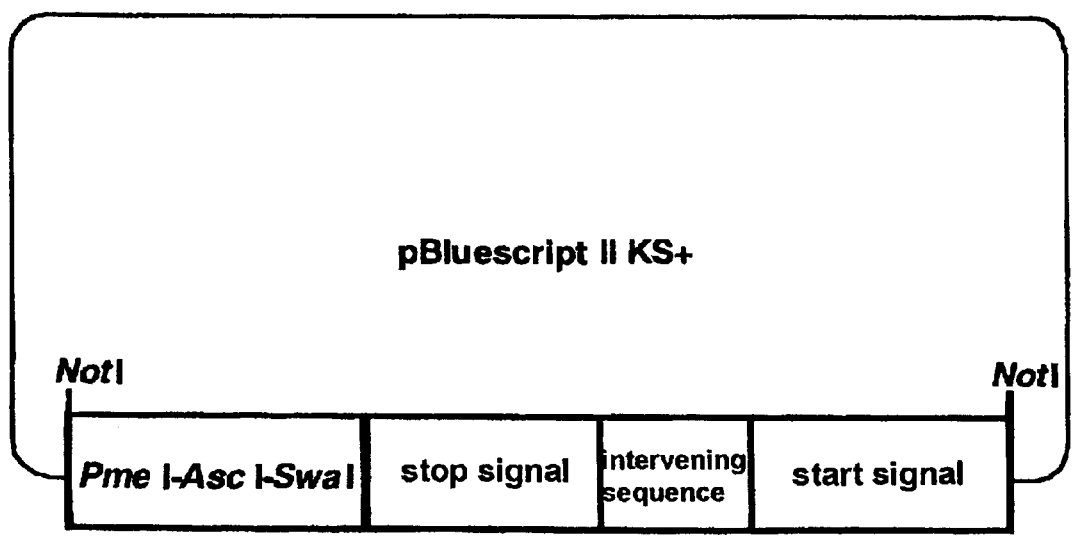
FIG. 2 shows structure of the cloning plasmid for adding, a NotI site, transcription start signal, intervening sequence, and a transcription stop signal to SEAP.

Human secreted alkaline phosphatase (SEAP) was subcloned by PCR as a reporter gene for evaluating the expression level of the foreign gene. For the primers, a 5' primer to which AscI restriction enzyme site has been added: 5'-gcggcgcgccatgctgctgctgctgctgctgggcctg-3' (SEQ ID NO: 11), and a 3' primer: 5'-gcggcgcgcccttatcatgtctgctcgaagcggccggccg-3' (SEQ ID NO: 12) were synthesized, and PCR was done. Template was pSEAP-Basic (CLONTECH), and the enzyme was Pfu tourbo DNA polymerase (STRATAGENE). Following PCR, products were digested with AscI, and purified/collected by electrophoresis. A synthetic double-stranded DNA [sense strand: 5'-gcggccgcgtttaaacggcgcgccatttaaatccgtagtaagaa aaacttagggtgaaagttcatcgcggccgc-3' (SEQ ID NO: 13), antisense strand: 5' gcggccgcgatgaactttcac-cctaagttttcttactacggatttaaatggcgcgccgtt aaacgcggccgc-3' (SEQ ID NO: 14)] comprising a multicloning site (PmeI-AscI-SwaI) and stop signal-intervening sequence-start signal was incorporated into the NotI site of pBluescript II+ to make the plasmid that will be subcloned (FIG. 2). The PCR product purified/recovered was ligated into the AscI site of this plasmid and cloned. After this was digested by NotI, the SEAP gene fragment was recovered/purified by electrophoresis and ligated to the above-mentioned five types of Sendai virus genomic cDNA and NotI site of pSeV18+. These viral vectors were respectively named, pSeV(+)NPP/ SEAP, pSeV(+)PM/SEAP, pSeV(+)MF/SEAP, pSeV(+) FHN/SEAP, pSeV(+)HNL/SEAP and pSeV18(+)/SEAP.

2. Reconstitution of the Virus $2 \times 10^6$ cells/dish LLC-MK2 cells were plated in a 100-mm dish, cultivated for 24 hours, and infected with psoralen and UV-treated T7 polymerase-expressing recombinant vaccinia virus (PLWUV-VacT7) (Fuerst, T. R. et al., Proc. Natl. Acad. Sci. USA 83: 8122–8126, 1986, Kato, A. et al., Genes Cells 1: 569–579, 1996) at room temperature, moi=2 for one hour. After washing the cells, each Sendai virus cDNA which had incorporated SEAP, pGEM/NP, pGEM/P, and pGEM/L, were suspended in 12 μg, 4 μg, 2 μg, and 4 μg/dish OptiMEM (GIBOCO BRL), 110 μl of SuperFect transfection reagent (QIAGEN) was added and mixed, after leaving at room temperature for 15 min, and ultimately, 3 ml OptiMEM containing 3% FBS was added to the cells and incubated for 3 to 5 hours. After the culture, the cells were washed twice with serum-free MEM, and cultured for a further 72 hours in MEM containing cytosine-β-D-arabinoflanoside (Arac). Then, cells were collected, the pellet was suspended in 1 ml PBS, and freeze thawing was repeated three times. 100 μl of this was inoculated into hen-eggs incubated for 10 days, the eggs were again incubated for 3 days at 35° C., and the chorio-allantoic fluid was collected. To make vaccinia-virus free, the collected chorio-allantoic fluids were diluted $10^{-5}$ to $10^{-7}$ and were re-inoculated into hen-eggs, re-collected similarly, was divided and stocked at –80° C. The respective viral vectors were named SeVNPP/SEAP, SeVPM/SEAP, SeVMF/SEAP, SeVFHN/SEAP, SeVHNL/SEAP and SeV18/SEAP).

3. Determination of Titer by Plaque Assay

Figure 4:
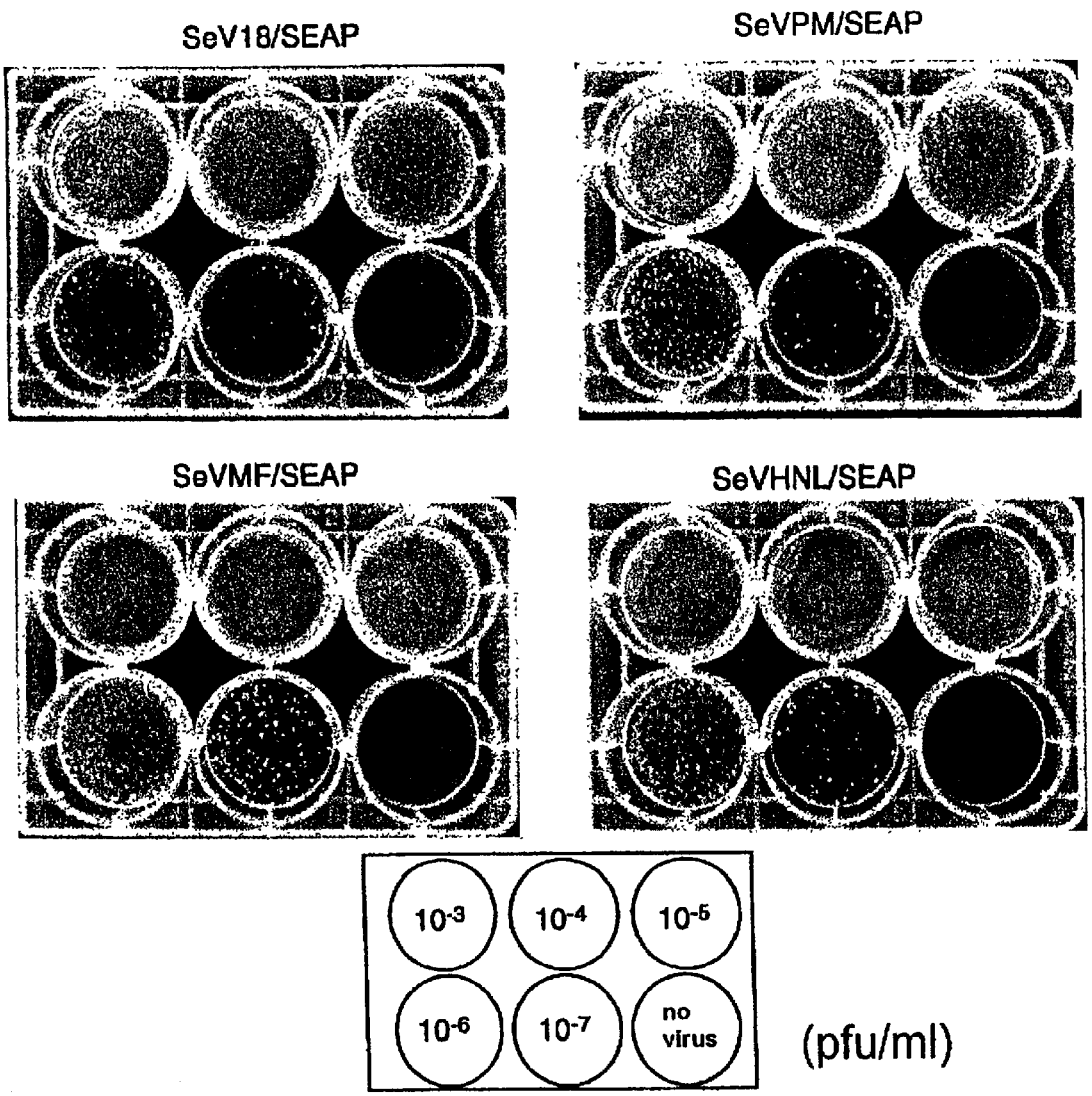
FIG. 4 shows the results of a plaque assay for each Sendai virus vector, showing a part of the fluorescent image of the plaque assay captured by LAS1000.
Figure 5:
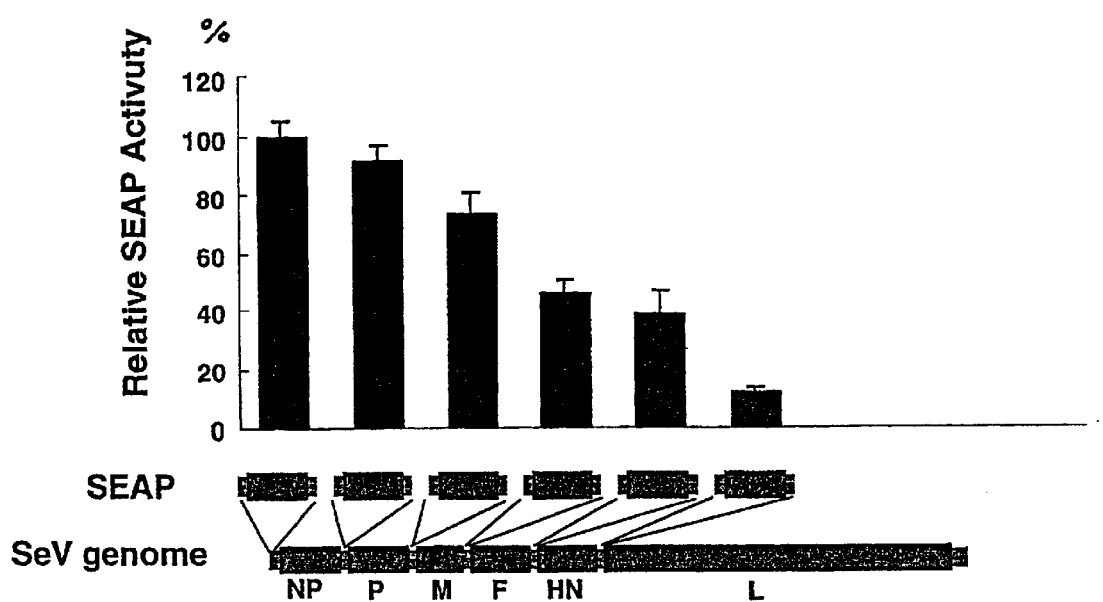
FIG. 5 compares the reporter gene (SEAP) expression levels of each Sendai virus vector. The relative value of each is shown taking SeV18+/SEAP data as 100. It was found that the activity, namely expression level of SEAP gene dropped as its location moved downstream.

CV-1 cells were plated onto a 6-well plate at $5 \times 10^5$ cells/well, and cultured for 24 hr. After washing the wells by PBS, recombinant SeV diluted $10^{-3}$, $10^{-4}$, $10^{-5}$, $10^{-6}$, $10^{-7}$ with with BSA/PBS (1% BSA in PBS) was added, and the plate was incubated for one hour. Then, the wells were washed with PBS, overlayered with 3 ml/well of BSA/ MEM/agarose (2% agarose mixed with 0.2% BSA+2×MEM of an equivalent weight), and incubated for 6 days at 37° C., 0.5%. After the culture, 3 ml of ethanol/acetic acid (ethanol:acetic acid=1:5) was added, set aside for 3 hours, and then the ethanol/acetic acid was removed together with agarose. The wells were washed again with PBS three times, incubated for one hour with 100 times-diluted rabbit anti-Sendai virus antibody, washed three times with PBS, incubated again for one hour with 200 times diluted Alexa Flour™-labeled goat anti-rabbit Ig(G+H) (Molecular Probe) at room temperature. Then, the wells were washed again with PBS three times, and florescent images were taken by luminoimage analyzer LAS1000(Fuji Film) to analyze plaques. The result is shown in FIG. 4. Table 1 shows the results of the titer obtained by this analysis.

TABLE 1

Recombinant Sendai viral titer measured by plaque assay

| Recombinant virus | Titer (pfu/ml) |
| --- | --- |
| SeV18/SEAP | $3.9 \times 10^9$ |
| SeVNPP/SEAP | $4.7 \times 10^8$ |
| SeVPM/SEAP | $3.8 \times 10^9$ |
| SeVMF/SEAP | $1.5 \times 10^{10}$ |
| SeVFHN/SEAP | $7.0 \times 10^9$ |
| SeVHNL/SEAP | $7.1 \times 10^9$ |

4. Comparison of Reporter Gene Expression $1 \times 10^5$ to $5 \times 10^5$ cells/well LLC-MK2 cells were plated on a 6-well plate, cultured for 24 hr, infected with each viral vector at moi=2, 100 μl of culture supernatant was collected after a 24-hr culture, and SEAP assay was conducted. The assay was done by the Reporter Assay Kit —SEAP— (Toyobo), and measured using luminoimage analyzer LAS1000 (Fuji Film). Each of the measured values was shown relatively taking the value of SeV18+/SEAP as 100. As a result, SEAP activity was detected in all cases where SEAP gene was inserted. It was found that SEAP activity decreased, in other words, the level of expression decreased, as the site of insertion neared the downstream of the genome. Also, when SEAP gene was inserted between NP gene and P gene, the expression level was in the mid-point of the expression level obtained by the vector in which the SEAP gene was inserted downstream of NP gene, and the expression level obtained by the vector in which the SEAP gene was inserted between P gene and M gene. ps 5. Preparation of the Multicloning Site A multicloning site SeV was added to the vector. The following two methods were used.

Figure 6:
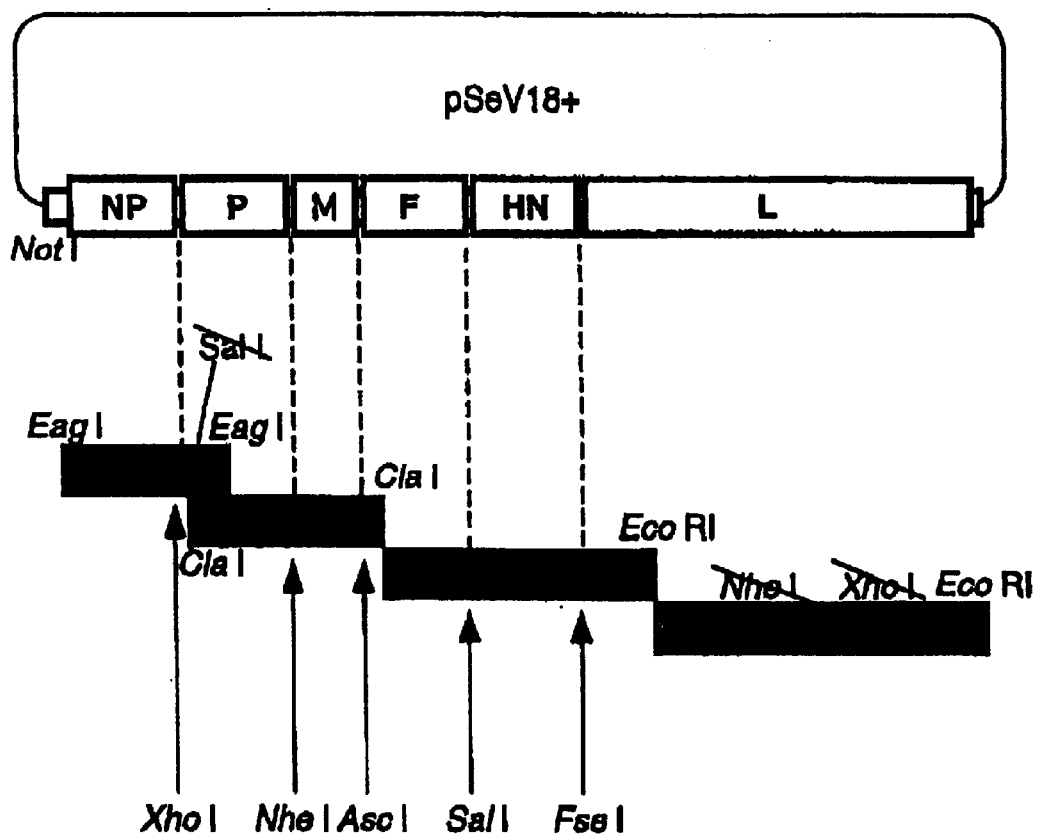
FIG. 6 shows the structure of the multicloning site.

1) Several restriction enzyme sites within Sendai virus (SeV) full length genomic cDNA, pSeV18+ b(+) (Hasan, M. K. et al., 1997, J. General Virology 78: 2813–2820)("pSeV18+ b(+)" is also called "pSeV18+") cDNA were destroyed, and new restriction enzyme sites containing the destroyed restriction enzyme sites were inserted between the start signal and ATG translation start signal of each gene (FIG. 6).

2) A multicloning site sequence and transcription start signal-intervening sequence-stop signal are added onto the already constructed SeV vector cDNA, and incorporated into the NotI site (FIG. 7).

In the case of 1), the method of transfection is as follows. First, as FIG. 6 (A), the fragment obtained by digesting pSeV18+ by EagI (2644 bp), the fragment digested by ClaI (3246 bp), the fragment digested by ClaI/EcoRI (5146 bp), and the fragment digested by EcoRI (5010 bp) were each separated by agarose electrophoresis, the corresponding bands were excised, and recovered/purified by QIAEXII Gel Extraction System (QIAGEN). The fragment digested by EagI was ligated to LITMUS38 (NEW ENGLAND BIOLABS), the fragment digested by ClaI, the fragment digested by ClaI/EcoRI, and the fragment digested by EcoRI was ligated to pBluescript II KS+ (STRATAGENE) and subcloned. Next, QuikChange Site-Directed Mutagenesis kit (STRATAGENE) was used to destroy restriction enzyme sites and carry out transfection.

The following primer sets were synthesized and used:

SalI sense strand: 5'-ggagaagtctcaacaccgtccacccaagataatc gatcag-3' (SEQ ID NO: 15), antisense strand: 5'-ctgatcgattatcttgggtggacggtgttgagac ttctcc-3' (SEQ ID NO: 16);

NheI sense strand: 5'-gtatatgtgttcagttgagcttgctgtcggtc taaggc-3' (SEQ ID NO: 17), antisense strand: 5'-gccttagaccgacagcaagctcaactgaacac atatac-3' (SEQ ID NO: 18);

XhoI sense strand: 5'-caatgaactctctagagaggctggagtcactaaagagtt acctgg-3' (SEQ ID NO: 19), antisense strand: 5'-ccaggtaactctttagtgactccagcctctctagagagt tcattg-3' (SEQ ID NO: 20);

For between NP-P sense strand: 5'-gtgaaagttcatccaccgatcggct- cactcgaggccacacccaacccaccg-3' (SEQ ID NO: 21), antisense strand: 5'-cggtggggttgggtgtggcctcgagt- gagccgatcggtggatgaactttcac-3' (SEQ ID NO: 22);

For between P-M sense strand: 5'-cttagggtgaaagaaatttcagctagcacggcgcaatggca gatatc-3' (SEQ ID NO: 23), antisense strand: 5'-gatatctgccattgcgccgtgctagctgaaatttctttcac cctaag-3' (SEQ ID NO: 24);

For between M-F sense strand: 5'-cttagggataaagtcccttgtgcgcgcttggttgcaaaact ctcccc-3' (SEQ ID NO: 25), antisense strand: 5'-ggggagagttttgcaaccaagcgcgcacaagggactttatc cctaag-3' (SEQ ID NO: 26);

For between F-HN sense strand: 5'-ggtcgcgcggtactttagtcgacacctcaaacaagcacaga tcatgg-3' (SEQ ID NO: 27), antisense strand: 5'-ccatgatctgtgcttgtttgaggtgtcgactaaagtaccgc gcgacc-3' (SEQ ID NO: 28;

For between HN-L sense strand: 5'-cccagggtgaatgggaagggccggccaggtcatggatgggcag gagtcc-3' (SEQ ID NO: 29), antisense strand: 5'-ggactcctgcccatccatgacctggccggccttcccattcac cctggg-3' (SEQ ID NO: 30).

After the transfection, each of the fragments were collected/purified as mentioned above, and cDNA were assembled (FIG. 6(B)).

In the case of 2), sense strand: 5'-ggccgcttaattaacggt ttaaacgcgcgccaacagtgttgataagaaaaacttagggtgaaagttcatcac-3' (SEQ ID NO: 31), antisense strand: 5'-ggccgtgatgaactt tcaccctaagttttctttatcaacactgttggcgcgcgtttaaaccgttaattaagc-3' (SEQ ID NO: 32) were synthesized, each of the synthesized DNAs were phosphorylated, annealed at 85° C. for 2 min, 65° C. for 15 min, 37° C. for 15 min, and room temperature for 15 min, and incorporated into SeV cDNA. Alternatively, multicloning sites of pUC18 or pBluescript II, and such plasmids, can be subcloned by PCR using a primer containing stop signal-intervening sequence-start signal, and this can be incorporated into SeV cDNA. The viral reconstitution of the cDNA made can be done as described above.

What is claimed is:

1. A replicable Sendai virus vector carrying a foreign gene that is positioned 5' to a gene encoding a viral protein in the negative strand genomic RNA contained within said vector, and wherein said RNA comprises an additional E-I-S sequence between said foreign gene and its 5'- or 3'-flanking gene encoding a viral protein.

2. The vector of claim 1, wherein said vector is selected from the group consisting of the vectors of (a) to (f) below, (a) a vector in which the foreign gene is inserted between the $1^{st}$ gene encoding a viral protein and the $2^{nd}$ gene encoding a viral protein from the 3' end of the negative strand genomic RNA contained within the vector;

(b) a vector in which the foreign gene is inserted between the $2^{nd}$ gene encoding a viral protein and the $3^{rd}$ gene encoding a viral protein from the 3' end of the negative strand genomic RNA contained within the vector;

(c) a vector in which the foreign gene is inserted between the $3^{rd}$ gene encoding a viral protein and the $4^{th}$ gene encoding a viral protein from the 3' end of the negative strand genomic RNA contained within the vector;

(d) a vector in which the foreign gene is inserted between the $4^{th}$ gene encoding a viral protein and the $5^{th}$ gene encoding a viral protein from the 3' end of the negative strand genomic RNA contained within the vector;

(e) a vector in which the foreign gene is inserted between the $5^{th}$ gene encoding a viral protein and the $6^{th}$ gene encoding a viral protein from the 3' end of the negative strand genomic RNA contained within the vector; and (f) a vector in which the foreign gene is inserted between the 6$^{th}$ gene encoding a viral protein from the 3' end of the negative strand genomic RNA contained within the vector, and the 5' end of said negative strand genomic RNA.

3. The vector of claim 2, wherein the 1$^{st}$ to 6$^{th}$ genes encoding viral proteins, counting from the 3' end to the 5' end of the negative strand genomic RNA contained within the vector, are in the following order: NP gene, P gene, M gene, F gene, HN gene, and L gene.

4. An isolated DNA corresponding to (a) the negative strand genomic RNA contained in the vector of claim 1 or (b) the complementary RNA of said negative strand genomic RNA.

5. A vector DNA carrying the DNA of claim 4 in an expressible manner.

6. The vector DNA of claim 5, which transcribes positive strand genomic RNA.

7. The vector of claim 1, wherein said additional E-I-S sequence is located between said foreign gene and its 5'-flanking gene encoding a viral protein in said negative strand genomic RNA.

8. The vector of claim 1 or 7, wherein said additional E-I-S sequence comprises the corresponding RNA sequence of SEQ ID NO:33.

9. A composition comprising at least 4.7×10$^8$ pfu/ml of the replicable Sendai virus vector of claim 1 in a physiologically acceptable vehicle.

* * * * *

UNITED STATES PATENT AND TRADEMARK OFFICE
CERTIFICATE OF CORRECTION

PATENT NO. : 6,746,860 B1
DATED : June 8, 2004
INVENTOR(S) : Tsuyoshi Tokusumi et al.

It is certified that error appears in the above-identified patent and that said Letters Patent is hereby corrected as shown below:

Title page,
Item [56], References Cited, OTHER PUBLICATIONS, please replace "Schnell et al., "Infectious rabies from cloned cDNA," *EMBO Journal* 13:4195-4203 (1994)." with -- Schnell et al., "Infectious rabies viruses from cloned cDNA," *EMBO Journal* 13:4195-4203 (1994). --.
Item [73], Assignee, please replace "DNAVEC Research, Inc., Tsukuba" with -- DNAVEC Research, Inc., Ibaraki (JP) --.

Signed and Sealed this

Twenty-second Day of February, 2005

JON W. DUDAS
*Director of the United States Patent and Trademark Office*

SEQUENCE LISTING

<160> NUMBER OF SEQ ID NOS: 34

<210> SEQ ID NO 1
<211> LENGTH: 41
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 1
ccaccgacca cacccagcgg ccgcgacagc cacggcttcg g                41

<210> SEQ ID NO 2
<211> LENGTH: 41
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 2
ccgaagccgt ggctgtcgcg gccgctgggt gtggtcggtg g                41

<210> SEQ ID NO 3
<211> LENGTH: 40
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 3
gaaatttcac ctaagcggcc gcaatggcag atatctatag                 40

<210> SEQ ID NO 4
<211> LENGTH: 40
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 4
ctatagatat ctgccattgc ggccgcttag gtgaaatttc                 40

<210> SEQ ID NO 5
<211> LENGTH: 43
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 5
gggataaagt cccttgcggc cgcttggttg caaaactctc ccc             43

<210> SEQ ID NO 6
<211> LENGTH: 43
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 6

```
ggggagagtt ttgcaaccaa gcggccgcaa gggactttat ccc                    43
```

<210> SEQ ID NO 7
<211> LENGTH: 47
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 7

```
ggtcgcgcgg tactttagcg gccgcctcaa acaagcacag atcatgg                 47
```

<210> SEQ ID NO 8
<211> LENGTH: 47
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 8

```
ccatgatctg tgcttgtttg aggcggccgc taaagtaccg cgcgacc                 47
```

<210> SEQ ID NO 9
<211> LENGTH: 44
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 9

```
cctgcccatc catgacctag cggccgcttc ccattcaccc tggg                    44
```

<210> SEQ ID NO 10
<211> LENGTH: 44
<212> TYPE: DNA
<213> ORGANISM: Artificial Sequence
<220> FEATURE:
<223> OTHER INFORMATION: Artificially synthesized sequence derived from
      the Sendai virus

<400> SEQUENCE: 10

```
cccagggtga atgggaagcg gccgctaggt catggatggg cagg                    44
```

<210> SEQ ID NO 11
<211> LENGTH: 40
<212> TYPE: DNA
<213> ORGANISM: Artificial Sequence
<220> FEATURE:
<223> OTHER INFORMATION: Artificially synthesized sequence derived from
      human secreted alkaline phosphatase

<400> SEQUENCE: 11

```
gcggcgcgcc atgctgctgc tgctgctgct gctgggcctg                         40
```

<210> SEQ ID NO 12
<211> LENGTH: 40
<212> TYPE: DNA
<213> ORGANISM: Artificial Sequence
<220> FEATURE:
<223> OTHER INFORMATION: Artificially synthesized sequence derived from
      human secreted alkaline phosphatase

<400> SEQUENCE: 12

-continued

```
gcggcgcgcc cttatcatgt ctgctcgaag cggccggccg                        40

<210> SEQ ID NO 13
<211> LENGTH: 74
<212> TYPE: DNA
<213> ORGANISM: Artificial Sequence
<220> FEATURE:
<223> OTHER INFORMATION: Artificially synthesized sequence containing a
      multicloning site

<400> SEQUENCE: 13
gcggccgcgt ttaaacggcg cgccatttaa atccgtagta agaaaaactt agggtgaaag    60
ttcatcgcgg ccgc                                                      74

<210> SEQ ID NO 14
<211> LENGTH: 74
<212> TYPE: DNA
<213> ORGANISM: Artificial Sequence
<220> FEATURE:
<223> OTHER INFORMATION: Artificially synthesized sequence containing a
      multicloning site

<400> SEQUENCE: 14
gcggccgcga tgaactttca ccctaagttt ttcttactac ggatttaaat ggcgcgccgt    60
ttaaacgcgg ccgc                                                      74

<210> SEQ ID NO 15
<211> LENGTH: 40
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 15
ggagaagtct caacaccgtc cacccaagat aatcgatcag                          40

<210> SEQ ID NO 16
<211> LENGTH: 40
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 16
ctgatcgatt atcttgggtg gacggtgttg agacttctcc                          40

<210> SEQ ID NO 17
<211> LENGTH: 38
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 17
gtatatgtgt tcagttgagc ttgctgtcgg tctaaggc                            38

<210> SEQ ID NO 18
<211> LENGTH: 38
<212> TYPE: DNA
<213> ORGANISM: Artificial Sequence
<220> FEATURE:
<223> OTHER INFORMATION: Artificially synthesized sequence for use in
      site directed mutagenesis of the Sendai virus
```

```
<400> SEQUENCE: 18
gccttagacc gacagcaagc tcaactgaac acatatac                          38

<210> SEQ ID NO 19
<211> LENGTH: 45
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 19
caatgaactc tctagagagg ctggagtcac taaagagtta cctgg                  45

<210> SEQ ID NO 20
<211> LENGTH: 45
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 20
ccaggtaact ctttagtgac tccagcctct ctagagagtt cattg                  45

<210> SEQ ID NO 21
<211> LENGTH: 52
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 21
gtgaaagttc atccaccgat cggctcactc gaggccacac ccaaccccac cg          52

<210> SEQ ID NO 22
<211> LENGTH: 52
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 22
cggtggggtt gggtgtggcc tcgagtgagc cgatcggtgg atgaactttc ac          52

<210> SEQ ID NO 23
<211> LENGTH: 47
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 23
cttagggtga agaaatttc agctagcacg gcgcaatggc agatatc                 47

<210> SEQ ID NO 24
<211> LENGTH: 47
<212> TYPE: DNA
<213> ORGANISM: Artificial Sequence
<220> FEATURE:
<223> OTHER INFORMATION: Artificially synthesized sequence for use in
      site directed mutagenesis of the Sendai virus
```

<400> SEQUENCE: 24
gatatctgcc attgcgccgt gctagctgaa atttctttca ccctaag                47

<210> SEQ ID NO 25
<211> LENGTH: 47
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 25
cttagggata aagtcccttg tgcgcgcttg gttgcaaaac tctcccc                47

<210> SEQ ID NO 26
<211> LENGTH: 47
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 26
ggggagagtt ttgcaaccaa gcgcgcacaa gggactttat ccctaag                47

<210> SEQ ID NO 27
<211> LENGTH: 47
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 27
ggtcgcgcgg tactttagtc gacacctcaa acaagcacag atcatgg                47

<210> SEQ ID NO 28
<211> LENGTH: 47
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 28
ccatgatctg tgcttgtttg aggtgtcgac taaagtaccg cgcgacc                47

<210> SEQ ID NO 29
<211> LENGTH: 49
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 29
cccagggtga atgggaaggg ccggccaggt catggatggg caggagtcc              49

<210> SEQ ID NO 30
<211> LENGTH: 49
<212> TYPE: DNA
<213> ORGANISM: Artificial Sequence
<220> FEATURE:
<223> OTHER INFORMATION: Artificially synthesized sequence for use in
      site directed mutagenesis of the Sendai virus

<400> SEQUENCE: 30

```
ggactcctgc ccatccatga cctggccggc ccttcccatt caccctggg          49

<210> SEQ ID NO 31
<211> LENGTH: 72
<212> TYPE: DNA
<213> ORGANISM: Artificial Sequence
<220> FEATURE:
<223> OTHER INFORMATION: Artificially synthesized sequence containing a
      multicloning site, a transcription start signal, and stop signal

<400> SEQUENCE: 31
ggccgcttaa ttaacggttt aaacgcgcgc caacagtgtt gataagaaaa acttagggtg    60
aaagttcatc ac                                                        72

<210> SEQ ID NO 32
<211> LENGTH: 72
<212> TYPE: DNA
<213> ORGANISM: Artificial Sequence
<220> FEATURE:
<223> OTHER INFORMATION: Artificially synthesized sequence containing a
      multicloning site, a transcription start signal,
      and stop signal

<400> SEQUENCE: 32
ggccgtgatg aactttcacc ctaagttttt cttatcaaca ctgttggcgc gcgtttaaac    60
cgttaattaa gc                                                        72

<210> SEQ ID NO 33
<211> LENGTH: 10
<212> TYPE: DNA
<213> ORGANISM: Artificial Sequence
<220> FEATURE:
<223> OTHER INFORMATION: Artificially Synthesized Sequence Containing
      the Sendai Virus S Sequence

<400> SEQUENCE: 33
ctttcaccct                                                           10

<210> SEQ ID NO 34
<211> LENGTH: 15
<212> TYPE: DNA
<213> ORGANISM: Artificial Sequence
<220> FEATURE:
<223> OTHER INFORMATION: Artificially Synthesized Sequence Containing
      the Sendai Virus E Sequence

<400> SEQUENCE: 34
tttttcttac tacgg                                                     15
```